(12) United States Patent
Wu et al.

(10) Patent No.: US 11,712,461 B2
(45) Date of Patent: Aug. 1, 2023

(54) LONG-ACTING POLYPEPTIDE COMPOSITION FOR TREATING ATRIAL FIBRILLATION AND ITS APPLICATION

(71) Applicants: Yue Wu, Xi'an (CN); Kaiyue Feng, Xi'an (CN); Chaofeng Sun, Xi'an (CN)

(72) Inventors: Yue Wu, Xi'an (CN); Kaiyue Feng, Xi'an (CN); Chaofeng Sun, Xi'an (CN)

(73) Assignee: THE FIRST AFFILIATED HOSPITAL OF XI'AN JIAOTONG UNIVERSITY, Xi'an (CN)

( * ) Notice: Subject to any disclaimer, the term of this patent is extended or adjusted under 35 U.S.C. 154(b) by 0 days.

(21) Appl. No.: 17/931,117

(22) Filed: Sep. 10, 2022

(65) Prior Publication Data

US 2023/0131922 A1 Apr. 27, 2023

(30) Foreign Application Priority Data

Sep. 16, 2021 (CN) .......................... 202111084913.2

(51) Int. Cl.
| | | |
|---|---|---|
| *A61K 38/16* | (2006.01) | |
| *A61P 9/06* | (2006.01) | |
| *C07K 14/00* | (2006.01) | |

(52) U.S. Cl.
CPC ................ *A61K 38/16* (2013.01); *A61P 9/06* (2018.01); *C07K 14/00* (2013.01)

(58) Field of Classification Search
CPC ........ A61K 38/16; A61K 38/00; C07K 14/00; A61P 9/00
See application file for complete search history.

(56) References Cited

U.S. PATENT DOCUMENTS

2009/0281019 A1 11/2009 Arora et al.
2013/0096050 A1 4/2013 Shandler

OTHER PUBLICATIONS

Ling Wei et al., "Serum type I and type III procollagen peptide and angiotensin-converting enzyme gene polymorphisms in elderly patients with non-valvular atrial fibrillation" Chinese Journal of Cardiac Pacing and Electrophysiology, 2008, vol. 22, No. 4, pp. 333-336.

(Continued)

*Primary Examiner* — Lianko G Garyu

(57) ABSTRACT

A polypeptide composition for treating atrial fibrillation includes a polypeptide that has a sequence: fADNYTRLRKQMAVKKYLNSILN-NH₂ (SEQ ID NO: 1), From an N-terminus of the polypeptide, a first amino acid (f) is a D-Phe, a second amino acid is Ala, and a third amino (Continued)

acid is Asp; and the peptide is linear in a solution and forms an α-helix structure after encountering a lipid bilayer.

5 Claims, 4 Drawing Sheets

Specification includes a Sequence Listing.

(56) References Cited

OTHER PUBLICATIONS

Chun-Ian Xu et al. "Recombinant expressed vasoactive intestinal peptide analogue ameliorates TNBS-induced colitis in rats" World J Gastroenterol Feb. 14, 2018; 24(6): 706-715 (Feb. 14, 2018).

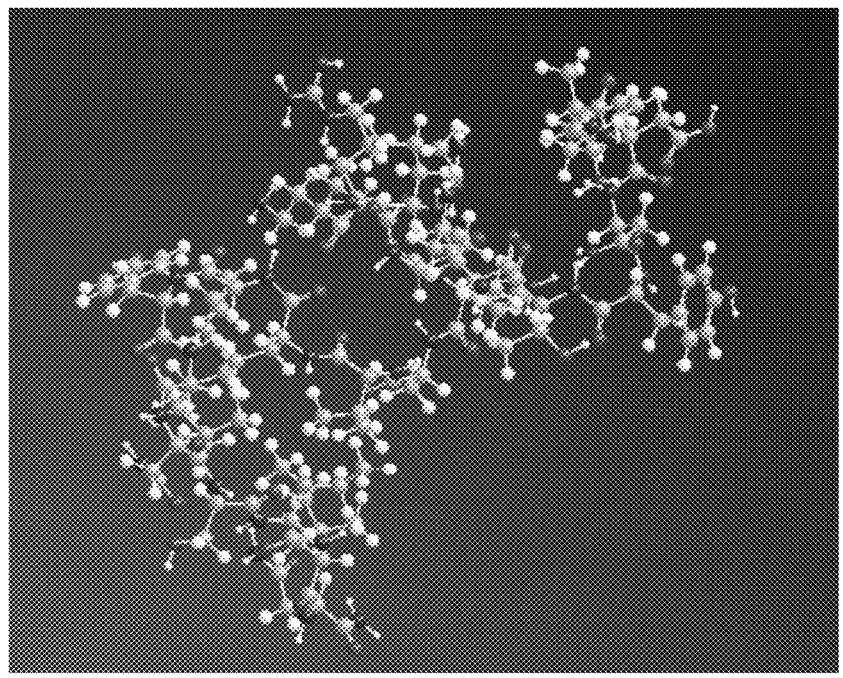
FIG. 1
FIG. 2
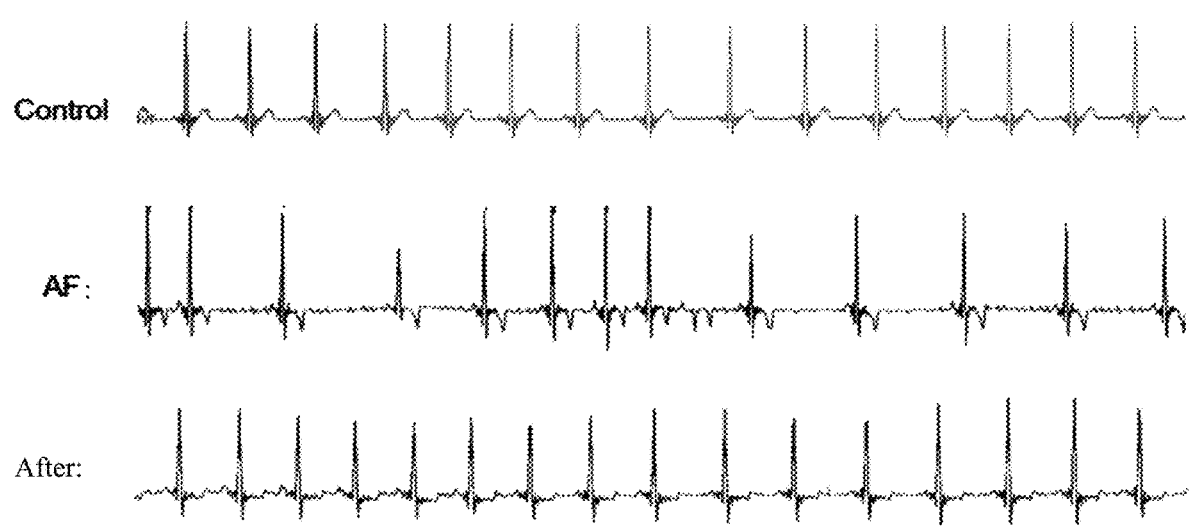

LONG-ACTING POLYPEPTIDE COMPOSITION FOR TREATING ATRIAL FIBRILLATION AND ITS APPLICATION

The present application claims priority to Chinese Patent Application No. 202111084913.2, filed on Sep. 16, 2021, which is incorporated by reference for all purposes as if fully set forth herein.

A Sequence Listing XML a file named "10025_0093.xml" created on Sep. 10, 2022, and having a size of 2,662 bytes, is filed concurrently with the specification. The sequence listing contained in the XML file is part of the specification and is herein incorporated by reference in its entirety.

TECHNICAL FIELD

The invention belongs to the technical field of biomedical technology, and particularly, relates to a long-acting polypeptide composition and its application to treat atrial fibrillation.

BACKGROUND TECHNIQUE

Atrial fibrillation is the most common clinical persistent arrhythmia. Epidemiological studies have shown that the total prevalence of atrial fibrillation in China can be as high as 0.77%, and it is positively correlated with age. The prevalence is 80 years old. It can be as high as 5% to 15%. At the same time, the occurrence of atrial fibrillation can increase the patient's risk of stroke by 5 times, the risk of heart failure by 3 times, the risk of dementia by 2 times, and the case fatality rate is even twice that of healthy people. Therefore, how to effectively treat atrial fibrillation has become a crucial issue faced by clinical and scientific researchers.

It is believed that the occurrence and development of atrial fibrillation may be related to multiple wave reentry and focal triggering in the atrium, activation of the RAAS system, remodeling of atrial structure, oxidative stress and inflammation, and cardiac autonomic nervous system (CANS). The main current treatment direction is to control the ventricular rate based on the etiology, to convert and maintain sinus rhythm, and to prevent the formation of thrombus. Specific methods include radiofrequency ablation, drug therapy, etc. Drugs include β-blockers that control ventricular rate; non-dihydropyridine calcium ion antagonists; Ic drugs that stop reentry excitement by slowing down the conduction velocity and extending the effective refractory period to stop reentry excitement; class III drugs for cardioversion of atrial fibrillation, etc. However, although there are many drugs, there are still a large number of patients with mediocre treatment results.

In recent years, it has been discovered that the onset of atrial fibrillation in some patients is closely related to the autonomic nervous system. Stimulating the vagus nerve plexus can significantly shorten the circumference of the pulmonary vein and intra-atrial fibrillation. For some patients, atrial fibrillation mostly occurs at night, at rest or during meals. Thus, atropine treatment is effective. The treatment of atrial fibrillation through the vagus nerve can be a new and important way.

SUMMARY OF THE INVENTION

In one embodiment, the present application discloses a polypeptide composition for treating atrial fibrillation including a polypeptide that has a sequence:

(SEQ ID NO: 1)
fADNYTRLRKQMAVKKYLNSILN-NH$_2$.

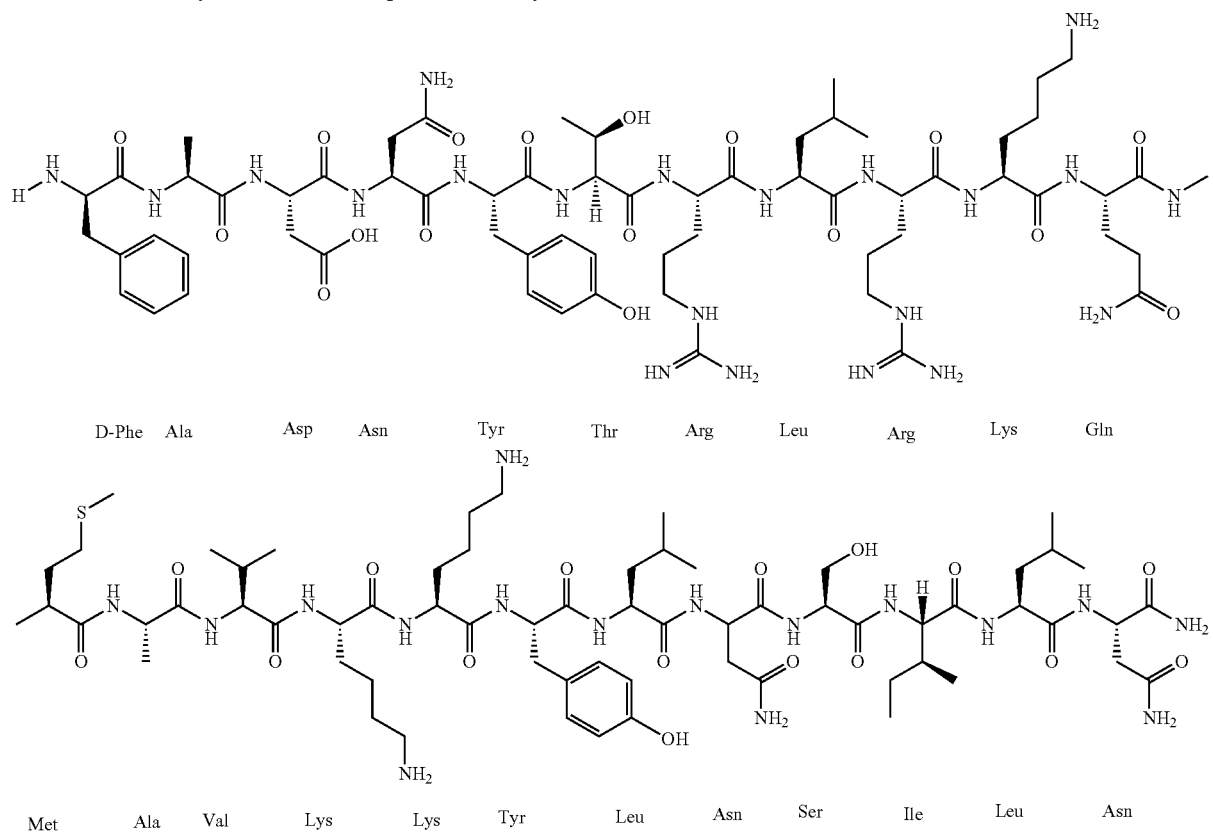

From an N-terminus of the polypeptide, a first amino acid (f) is a D-PHE, a second amino acid is Ala, and a third amino acid is Asp; and the polypeptide is linear in a solution and forms an α-helix structure after encountering a lipid bilayer.

In another embodiment, the polypeptide has an effect of treating atrial fibrillation by acting on an autonomic nervous system of a heart.

In another embodiment, the polypeptide reduces an occurrence of supraventricular premature beat events.

In another embodiment, the polypeptide reduces an occurrence of supraventricular tachycardia events.

In another embodiment, the polypeptide reverses atrial fibrillation and reduces an occurrence of arrhythmia events in a time-dependent manner.

The beneficial effects of the present invention are:

(1) By modifying amino acids and chemical synthesis, the half-life of the polypeptide is prolonged, and a polypeptide drug with a more stable spatial conformation and a longer effective time of action is obtained.

(2) The 24 hours electrocardiogram test proved that the long-acting polypeptide drug can affect the cardiac autonomic nervous system and achieve the effect of treating atrial fibrillation.

(3) Th polypeptide can simultaneously reduce the occurrence of arrhythmia events accompanied by atrial fibrillation in a time-dependent manner, and have good medical development value.

DESCRIPTION OF THE DRAWINGS

FIG. 1 shows the structure of Polypeptide VA.

FIG. 2 shows the comparison of the ECG of Beagle dogs before and after treatment with Peptide VA.

DETAILED DESCRIPTION

Figure 3:
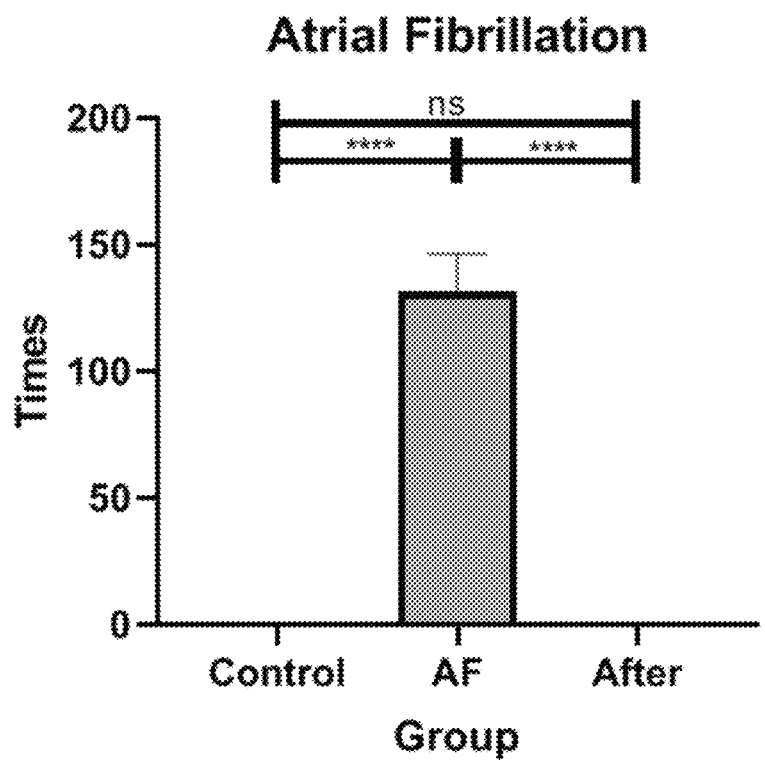
FIG. 3 shows the effect of Polypeptide VA on the frequency of atrial fibrillation before and after treatment.

The following examples facilitate a better understanding of the present invention, but do not limit the present invention. The experimental methods in the following examples, unless otherwise specified, are conventional methods. The experimental materials in the following examples, unless otherwise specified, are obtained from conventional biochemical reagent stores.

A long-acting polypeptide drug that can be used to treat atrial fibrillation. The amino acid sequence is fADNYTRLRKQMAVKKYLNSILN-NH$_2$.

Referring to FIG. 1, its structure is as follows:

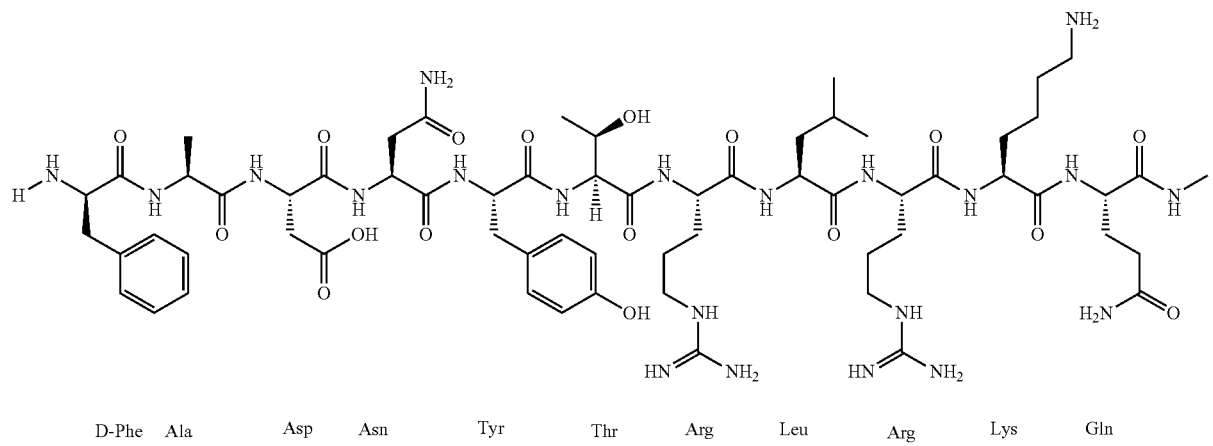

D-Phe  Ala  Asp  Asn  Tyr  Thr  Arg  Leu  Arg  Lys  Gln

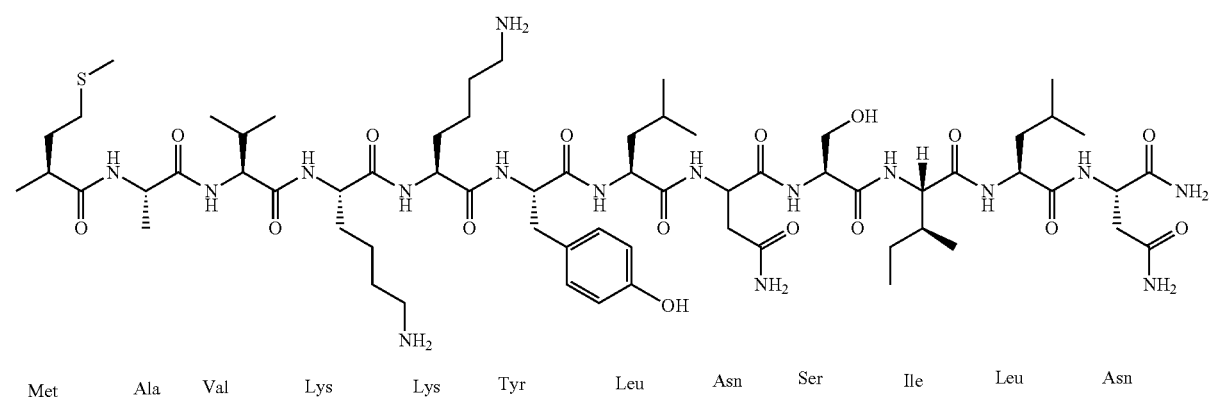

Met  Ala  Val  Lys  Lys  Tyr  Leu  Asn  Ser  Ile  Leu  Asn

In order to increase its stability, the N-terminal amino acid of this sequence is designed as a D-type amino acid, the second amino acid is Asp to increase its half-life, and then the amino acid Ala is connected to enhance the stability of enzymatic hydrolysis. At the same time, the polypeptide is linear in the solution. After encountering a lipid bilayer, α-helix can be formed with a more stable structure.

The chemical synthesis method: MBHA Resin as raw material; piperidine as deprotection reagent; TFA, TIS, EDT as lysis reagent; DMF, DCM, MEOH, DIEA, HBTU as synthesis reagents; DMF and DCM as washing reagents; phenol, pyridine, and ninhydrin as detection reagents: after resin swelling and deprotection, after the detection reagent was positive at 105° C.-110° C. (heating for 5 min, turning dark blue), washing and filtering out the solvent. The amino acids were connected in sequence through a polypeptide synthesizer, and finally drained. The resin was washed, and the polypeptide was cut from the resin. The cutting time was about 120 minutes, and then the lysate was blown dry as much as possible with nitrogen, washed with ether for six times, and then evaporated to dryness at room temperature for analysis. After purification, the polypeptide (Polypeptide VA) was freeze-dried into powder and stored in −80° C. refrigerator.

The identification of the function of the above-synthesized polypeptide for the treatment of atrial fibrillation includes the following steps:

(1) Establishing a large animal model: male beagle dogs from 12 to 18 months old, provided by the Animal Experimental Center of Xi'an Jiaotong University School of Medicine, using self-control method, real-time monitoring of beagle dog electrocardiogram through holter to determine whether atrial fibrillation occurred. And recording the baseline, the ECG when the atrial fibrillation occurred and after the polypeptide intervention.

(2) Establishing a small animal model: selecting atrial fibrillation model mice, using self-control methods, and comparing the intracardiac electrophysiological graphs of atrial fibrillation induced by S1S2 pacing before and after injecting to further measure the effect of the drug.

(3) Polypeptide treatment method: dissolving the polypeptide in physiological saline, and injecting $5*10^{-9}$ mol/kg into the loose subcutaneous tissue at the back of the beagle' neck every day, once a day, record the injection time, and record the injection continuously for 5 days.

(4) Electrocardiogram detection method: the large-scale detection indicators in this experiment were all carried out by holter (FIG. 2). Beagle dogs were anesthetized, their hair was shaved, and electrodes were attached. After the connection was established, the ECG monitoring was started.

The analysis of the efficacy of Polypeptide VA on atrial fibrillation in dogs with atrial fibrillation includes the following steps:

1) Polypeptide therapy for dogs with atrial fibrillation: daily injection of $5*10^{-9}$ mol/kg into the loose subcutaneous tissue at the back of the neck of the beagle dog, once a day, continuous injection and recording.

2) The electrocardiogram and atrial fibrillation events of dogs with atrial fibrillation were analyzed by Holter, and the electrocardiograms and atrial fibrillation events of normal dogs, atrial fibrillation dogs and beagle dogs treated with peptides were compared. GraphPad software was used for statistical analysis, and variance statistical T test was used.

The results are shown in FIGS. 2 and 3. The results show that: compared with the atrial fibrillation dogs that were not injected with the polypeptide, the dogs after treatment had obviously higher heart rate regularity, lower amount of arrhythmias, and lower amount of atrial fibrillation was greatly reduced, basically the same as normal dogs. It shows that the polypeptide has a better effect on the treatment of atrial fibrillation. At the same time, even if the subcutaneous injection is once a day, the drug still has a good therapeutic effect, which indicates that the polypeptide preparation has a long half-life and can be used as a long-acting drug for treatment.

Polypeptide VA can reduce the occurrence of arrhythmia events in Beagle dogs with atrial fibrillation:

1) Polypeptide therapy for dogs with atrial fibrillation: daily injection of $5*10^{-9}$ mol/kg into the loose subcutaneous tissue at the back of the neck of the beagle dog, once a day, continuous injection and recording.

2) Conducting electrocardiogram analysis on dogs with atrial fibrillation through Holter, comparing and analyzing the supraventricular premature beats and supraventricular tachycardia events of normal dogs, atrial fibrillation dogs and beagle dogs treated with polypeptide, using GraphPad software to perform statistical analysis on them, conducting variance statistical T test.

Figure 4:
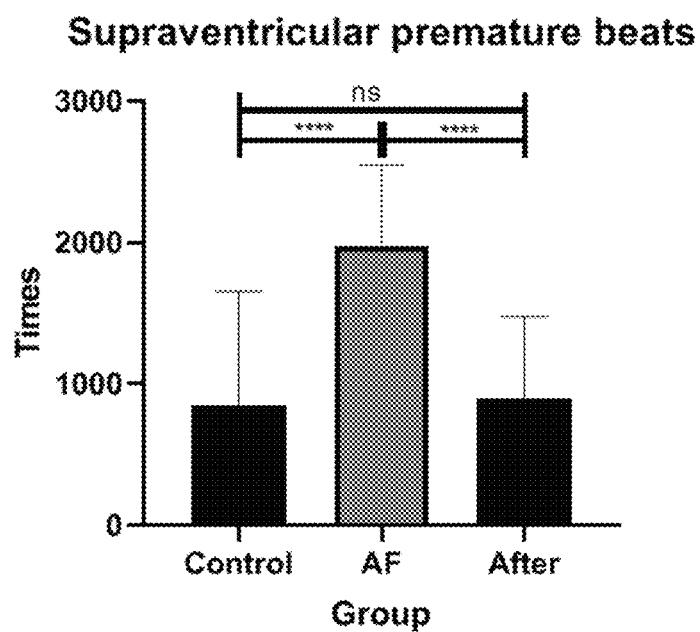
FIG. 4 The effect of Polypeptide VA on supraventricular premature beats before and after treatment.
Figure 5:
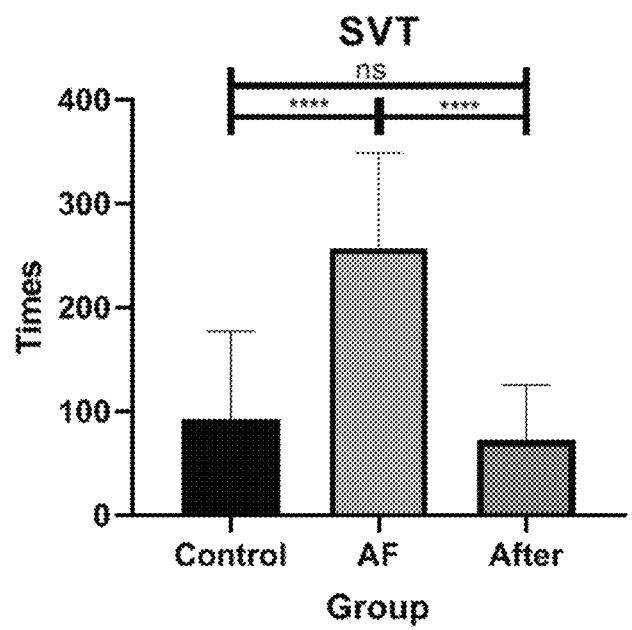
FIG. 5 shows the effect of Polypeptide VA on supraventricular tachycardia before and after treatment.

The results are shown in FIGS. 4 and 5. The results show that whether it is supraventricular premature beats or supraventricular tachycardia, the frequency of occurrence of atrial fibrillation in dogs can be reduced after treatment, and it can even be the same as normal dogs. It shows that the polypeptide can reduce the occurrence of arrhythmia events in dogs with atrial fibrillation.

Polypeptide VA reduces arrhythmia events in Beagle dogs with atrial fibrillation in a time-dependent manner.

1) Polypeptide therapy for dogs with atrial fibrillation: daily injection of $5*10^{-9}$ mol/kg into the loose subcutaneous tissue at the back of the neck of the beagle dog, once a day, continuous injection and recording.

2) Conducting electrocardiogram analysis on dogs with atrial fibrillation through holter, comparing and analyzing premature supraventricular contractions and supraventricular tachycardia events in dogs with atrial fibrillation on different days of drug administration, and using GraphPad software to perform statistical analysis on them, and conducting variance statistical T test.

Figure 6:
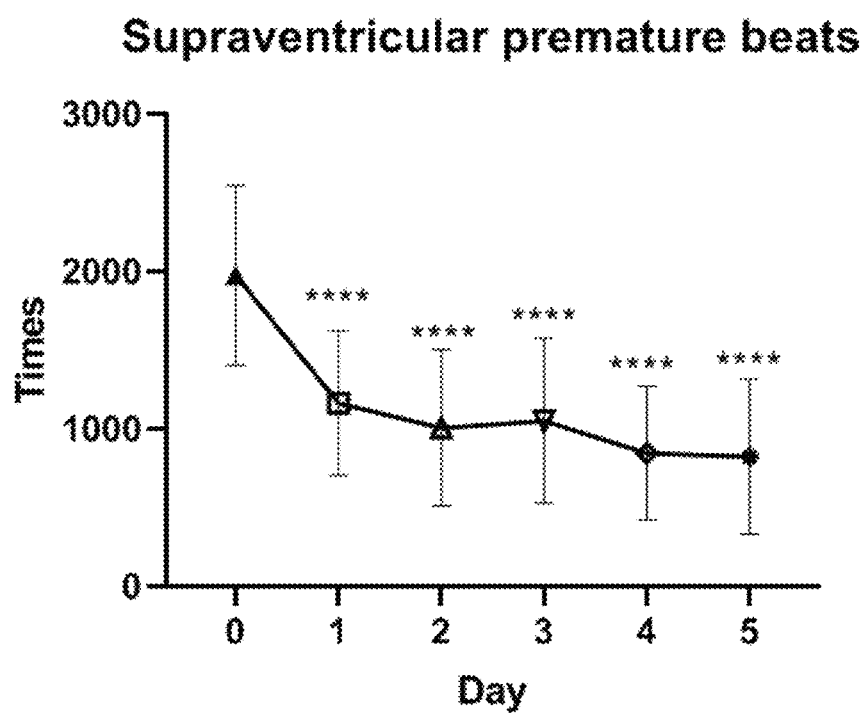
FIG. 6 shows the time-dependent effect of Polypeptide VA on supraventricular premature beats.
Figure 7:
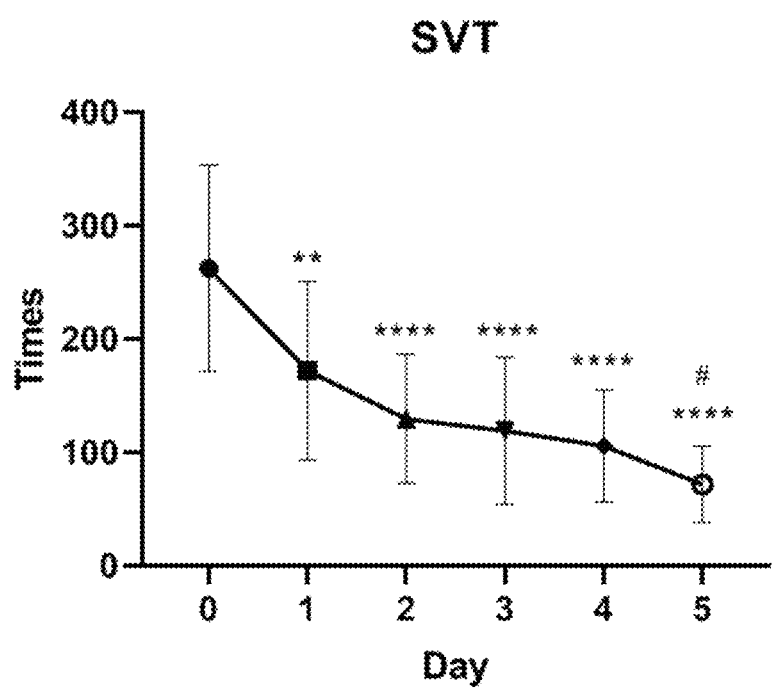
FIG. 7 shows the time-dependent effect of Polypeptide VA on supraventricular tachycardia.

The results are shown in FIGS. 6 and 7. The results show that whether it is a supraventricular premature contraction or supraventricular tachycardia, as the number of days of drug treatment increases, the dogs' arrhythmia events can be reduced. It shows that the polypeptide reduces arrhythmia events in dogs with atrial fibrillation in a time-dependent manner.

The analysis of the efficacy of Polypeptide VA on atrial fibrillation in atrial fibrillation mice includes the following steps:

1) To induce atrial fibrillation in mice: use programmed electrical stimulation, stimulate for 1 min, rest for 1 min, and record their intracardiac electrophysiological pictures for five cycles.

2) After intraperitoneal injection and spraying of the atrial fibrillation mice, the procedure was the same as the above, and the ECG of two times was recorded.

The results indicate that the RR interval heart rate of the atrial fibrillation mice after drug treatment was regular compared to the atrial fibrillation mice that were not injected with polypeptide, which indicates that the polypeptide has a better effect on the treatment of atrial fibrillation.

In summary, a long-acting polypeptide that can be used to treat atrial fibrillation can be used to treat atrial fibrillation by acting on the cardiac autonomic nervous system. The polypeptide can also reduce supraventricular fibrillation while treating atrial fibrillation. The occurrence of premature beat events and the occurrence of supraventricular tachycardia events are reduced. Atrial fibrillation in a time-dependent manner and the occurrence of accompanying arrhythmic events are also reduced.

The foregoing descriptions are only preferred embodiments of the present invention, and all equivalent changes and modifications made in accordance with the scope of the patent application of the present invention shall fall within the scope of the present invention.

The invention claimed is:

1. A polypeptide composition for treating atrial fibrillation comprising a polypeptide that has a sequence: fADNYTRLRKQMAVKKYLNSILN-NH$_2$ (SEQ ID NO: 1),

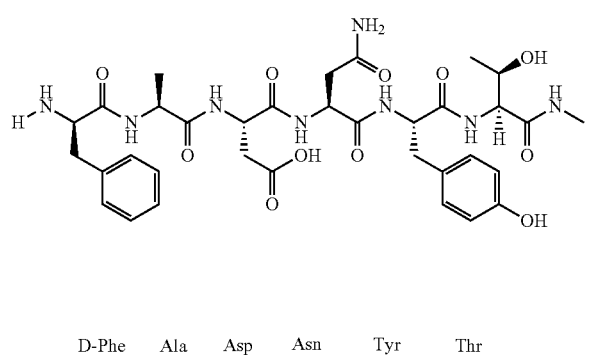

D-Phe    Ala    Asp    Asn    Tyr    Thr

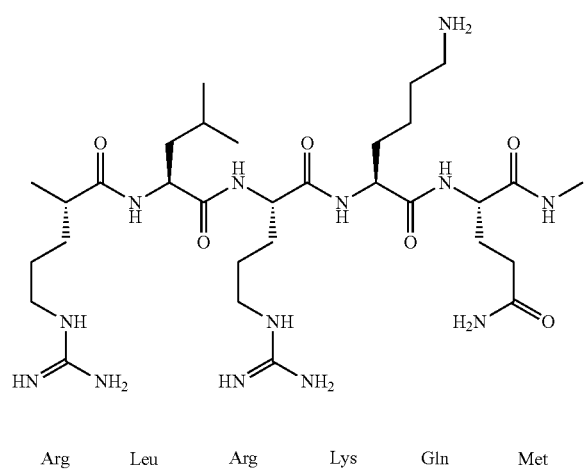

Arg    Leu    Arg    Lys    Gln    Met

-continued

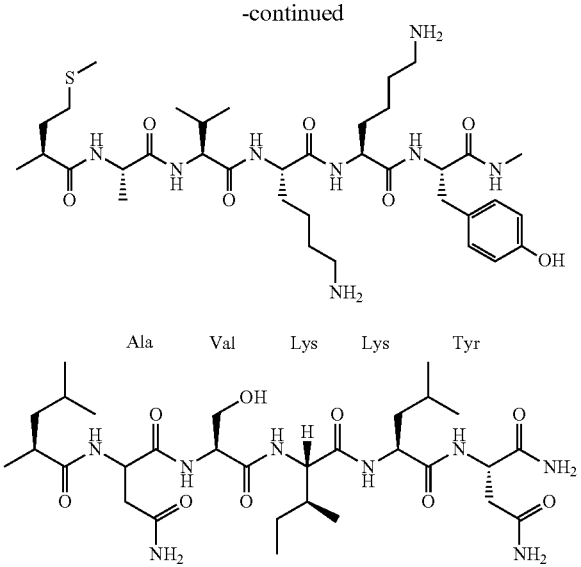

Ala    Val    Lys    Lys    Tyr

Leu    Asn    Ser    Ile    Leu    Asn wherein from an N-terminus of the polypeptide, a first amino acid (f) is a D-PHE, a second amino acid is Ala, and a third amino acid is Asp; and the peptide is linear in a solution and forms an α-helix structure after encountering a lipid bilayer.

2. The polypeptide composition according to claim 1, wherein the polypeptide has an effect of treating atrial fibrillation by acting on an autonomic nervous system of a heart.

3. The polypeptide composition according to claim 2, wherein the polypeptide reduces an occurrence of supraventricular premature beat events.

4. The polypeptide composition according to claim 2, wherein the polypeptide reduces an occurrence of supraventricular tachycardia events.

5. The polypeptide composition according to claim 2, wherein the polypeptide reverses atrial fibrillation and reduces an occurrence of arrhythmia events in a time-dependent manner.

* * * * *

SEQUENCE LISTING

```
Sequence total quantity: 1
SEQ ID NO: 1           moltype = AA  length = 23
FEATURE                Location/Qualifiers
REGION                 1..23
                       note = Polypeptide
MOD_RES                1
                       note = Phe is a D-amino acid
source                 1..23
                       mol_type = protein
                       organism = synthetic construct
SEQUENCE: 1
FADNYTRLRK QMAVKKYLNS ILN                                        23
```